United States Patent
Nicholson

(10) Patent No.: US 7,175,428 B2
(45) Date of Patent: Feb. 13, 2007

(54) SHAPE MEMORY SELF-LIGATING ORTHODONTIC BRACKETS

(76) Inventor: James A. Nicholson, 120 S. 28th Ave., Hattiesburg, MS (US) 39401

(*) Notice: Subject to any disclaimer, the term of this patent is extended or adjusted under 35 U.S.C. 154(b) by 179 days.

(21) Appl. No.: 10/882,165

(22) Filed: Jul. 2, 2004

(65) Prior Publication Data
US 2006/0003281 A1    Jan. 5, 2006

(51) Int. Cl.
A61C 3/00    (2006.01)
(52) U.S. Cl. .................... 433/11; 433/8; 433/10
(58) Field of Classification Search .......... 433/8–17
See application file for complete search history.

(56) References Cited

U.S. PATENT DOCUMENTS

| | | |
|---|---|---|
| 3,084,437 A | 4/1963 | Neger |
| 3,327,393 A | 6/1967 | Brader |
| 3,464,112 A | 9/1969 | Silverman |
| 3,855,701 A | 12/1974 | LeClair |
| 5,232,361 A | 8/1993 | Sachdeva |
| 5,356,289 A | 10/1994 | Watanabe |
| 6,302,688 B1 | 10/2001 | Jordan et al. |
| 6,509,094 B1 * | 1/2003 | Shah et al. ............ 428/395 |
| 6,554,612 B2 | 4/2003 | Georgakis |
| 6,582,226 B2 | 6/2003 | Jordan et al. |
| 6,663,385 B2 | 12/2003 | Tepper |

OTHER PUBLICATIONS

Packaging label of SmartClip™ by 3M Unitek, Monrovia CA 91016 (2004).

* cited by examiner

Primary Examiner—Cris L. Rodriguez
Assistant Examiner—Candice C. Stokes
(74) Attorney, Agent, or Firm—Dowell & Dowell, P.C.

(57) ABSTRACT

Self-ligating orthodontic brackets which are at least partially formed of materials exhibiting shape memory each of which includes a base from which extends two spaced and opposing pairs of tie wings each pair of which define an archwire guide slot therebetween. Each of the opposing tie wings include portions which are normally spaced to retain an archwire within the archwire guide slot but at least a portion of one of each pair of opposing tie wings is yieldable relative to the other to permit insertion and/or removal of the archwire relative to the archwire guide slot. Portions of the brackets may be coated to reduce friction between the archwire guide slot and the archwire and to promote aesthetics and overall bracket appearance.

23 Claims, 4 Drawing Sheets

SHAPE MEMORY SELF-LIGATING ORTHODONTIC BRACKETS

BACKGROUND OF THE INVENTION

1. Field of the Invention

This invention is generally directed to orthodontic brackets for use in aligning teeth and more specifically to self-ligating orthodontic brackets at least partially formed from shaped memory metallic alloys or non-metallic materials which include two pair of opposing tie wings which are spaced relative to one another along a base of each bracket and which serve to selectively and guidingly receive an archwire within archwire guide slots defined by each pair of opposing tie wings and posts.

2. Brief Description of Related Art

Generally, there are two basic styles of orthodontic brackets. A first style is known as a single wing wherein a pair of opposing elongated tie wings extend upwardly from a bracket base and are spaced to define an archwire guide slot therebetween. An example of a self-ligating single wing style bracket is disclosed in U.S. Pat. No. 6,663,385 to Tepper.

Twin brackets are the second style of brackets and have been developed to increase ease of bracket placement and use. Twin brackets include two pair of opposing tie wings which are spaced from one another with each pair defining an archwire guide slot therebetween. An example of such a bracket is described in U.S. Pat. No. 5,232,361 to Sachdeva et al. wherein the brackets are formed of titanium so as to be very hard and rigid. An example teaching away from a spaced pair of tie wings is disclosed in U.S. Pat. No. 5,356,289 to Watanabe wherein the brackets are formed of shape memory alloys or resins.

A variation of the twin bracket style has been developed to make the twin brackets self-ligating in order to avoid the necessity to tie-off the archwire used with the brackets. Such self-ligating twin brackets use supplemental hooks or latches which are mounted adjacent to each pair of tie wings for securely engaging or clamping an archwire. Unfortunately, the additional structure not only increases bracket costs and size, but also decreases bracket aesthetics and provides additional structure for trapping food and bacteria. An example of such a bracket is described in U.S. Pat. No. 6,554,612 to Georgakis et al.

Orthodontists are faced with many treatment difficulties as they bond orthodontic brackets to a patient's teeth and move them from crooked and irregular malocclusion positions to their ideal positions. The ideal alignment of teeth demands that they must be straight and aesthetical pleasing, but the teeth must also fit together correctly into normal occlusion and look and function in a superior clinical manner. There are a number of major challenges that Orthodontists must overcome to produce this superior clinical result.

There is often limited access to areas of the teeth where brackets must be placed to achieve normal orthodontic movement and produce superior treatment results. Useful areas may be small with access thereto very restricted, in which case, large brackets are not used successfully; whereas, smaller and compact twin type brackets can be placed in small areas and have enjoyed exceptional popularity among Orthodontists.

Ideal bracket placement on a patient's teeth is also necessary to produce ideal tooth alignment and achieve exceptional orthodontic results. To accomplish this necessary goal of ideal placement, brackets must often fit into small spaces between crooked and rotated teeth. A design feature of having a recessed point or horizontal groove located in the approximate center of the bracket will permit an Orthodontist to use a measuring device, such as a Boone Gauge, to precisely position brackets on teeth in exact desired positions.

Complete archwire engagement of the brackets on the teeth during various stages of orthodontic treatment is important but may not be possible. Many times, due to crooked alignment and closeness of the teeth, only two of the four bracket tie wings can be engaged at the same time. With single wing brackets or brackets without tie wings, it is extremely difficult to accomplish partial engagement successfully and this can result in an uncontrolled and unsatisfactory tooth movement. The true twin bracket design permits the engagement of at lease two of the opposing bracket tie wings to be used to begin tooth movement and, later in the treatment, two pair of opposing bracket tie wings can be used without compromising the patient's treatment.

The tooth movement process that is required to straighten teeth is very dynamic and constantly changing. The Orthodontist must have brackets that will accommodate the dynamics of tooth movement and not require replacement with new ones when a certain movement is required due to the difficulty of the patient's case.

Attachments such as Kobayashi hooks, metal ligatures, directional force elastics, elastomeric ties or elastomeric power chains are often used during various stages of orthodontic treatment. It is difficult to place such attachments on single wing style brackets and extremely difficult to place them on brackets without tie wings, however, a twin bracket configuration having four tie wings permits the Orthodontist to easily place such attachments and satisfactorily accomplish different aspects of a treatment.

Friction occurs as a normal part of tooth movement as a bracket and tooth slide along an archwire. This process is know as the sliding mechanics of orthodontics. The more points of contact between the archwire and a bracket slot during this process the greater the friction, which results in slower tooth movement and makes the treatment take longer. Elongated single wing brackets have increased friction resisting tooth movement and thus treatment is lengthy and more complicated to complete.

The aesthetic demands of the orthodontic patient are many and must be addressed to make the treatment acceptable to the patient. Smaller and less noticeable twin brackets are more aesthetic than larger single wing brackets and their aesthetics can be further improved. The true twin brackets allow the Orthodontists to attach colorful elastics, elastomeric ties, and power chain to the brackets that are pleasing to the patient.

A further major challenge to orthodontic treatment is the cleanliness of the brackets and areas where they are bonded or banded to the teeth. It is difficult for patients to clean areas adjacent to brackets and tooth surfaces. Bracket elements function as plaque traps that increase the chance of permanent stains, tooth decay, and gum disease. The use of larger single wings brackets makes it much harder for patients to keep their braces clean. The smaller twin designs are much easier for patients to clean and thus greatly reduced trapped food and are less likely to cause stains, tooth decay, or gum disease.

During the course of orthodontic treatment, archwires are placed and removed from the bracket/bracket slot as a normal part of treatment. Since most orthodontic brackets are made of stainless steel, both the bracket and bracket slots are rigid and inflexible. Once the archwire is placed in the bracket slot, it must be tied or ligated in place to prevent the archwire from coming out of the bracket and injuring the patient. The process of tying and untying every bracket to secure the archwire is a tedious and laborious procedure that must be repeated each time a new archwire is placed or removed. This process is time consuming and uncomfortable for the patient and inefficient for the Orthodontist. Self-ligating brackets have the advantage of using various mechanisms to secure archwires in the bracket slots without the need for metal or elastic ligatures. Because the current self-ligating brackets are not a true twin bracket design, they have serious limitations such that they are bulky and cumbersome to use in the small confines of the oral cavity.

In the 1980's nickel-titanium was introduced to orthodontics in the form of archwires with the trademark name of Nitinol™. The flexibility, shape memory effect, and superelasticity of Nitinol™ archwires offered a new wire that could be deflected to engage misaligned teeth and would return to its original form thereby straightening the teeth. The flexibility, shape memory effect, and superelastic nickel-titanium material has not, however, been used to construct a true twin bracket that looks and is shaped like the traditional stainless steel twin brackets.

SUMMARY OF THE INVENTION

This invention is directed to orthodontic brackets of the twin tie wing style wherein each bracket includes a base from which extends two pair of opposing tie wings. Each tie wing includes a post and a head portion with each pair of opposing posts defining an archwire guide slot therebetween of a dimension between approximately 0.018" to 0.022" to slidingly receive an archwire. The head portions include opposing inner flanges which are spaced closely adjacent to one another, or touch, in a normal position so as to prevent unplanned removal of an archwire seated within the archwire guide slot between the tie wings. Each head portion further includes an outwardly extending flange of the tie wing which may be used in a conventional manner for use in securing archwires with ligating wires or for adding other attachments which may be required during a patient's treatment.

In the present invention, at least one of each pair of opposing tie wings of the bracket is formed of a shape memory metallic alloy or non-metallic resin or polymer type material, such as a nickel-titanium alloy material, such that at least one tie wing of the bracket exhibits some degree of flexibility and shape memory. Thus, at least one of the opposing tie wings may be flexed such that the head portions of the opposing tie wings may separate to a distance to permit the insertion and/or removal of an archwire relative to the archwire guide slot defined therebetween. The nickel-titanium alloy or other material exhibiting a shape memory causes the tie wing or wings to return to a pre-determined position after an archwire is either inserted into or removed from the slot between the tie wings and posts. In preferred embodiments, each of the opposing tie wings is formed of a shape memory material so that each tie wing may be flexed to permit insertion and/or removal of an archwire from the archwire guide slots.

The two pair of opposing tie wings are spaced from one another and extend from the front surface of the bracket base such that the archwire slots are generally axially aligned relative to one another. In preferred embodiments of the invention, either a recessed point or horizontal groove is provided at or along the approximate center of each bracket base for purposes of precision alignment of the bracket with respect to a tooth using an instrument such as Boone gauge.

To reduce friction between an archwire and the orthodontic brackets of the present invention, the brackets, except the bonding mesh pads thereof, may be coated with a polytetrafluoroethylene (PTFE) material such as Teflon™, thermosetting polymer or other polymeric coatings with or without a coupling agent which form a smooth surface between the bracket and an archwire. To promote adherence of the coating, the brackets may be physically treated such as by a blasting process, chemical etching or the like. Archwires associated with the brackets of the present invention may also be similarly coated.

As opposed to plastic or polymer coatings, the brackets of the present invention may be plated or electroplated with a metallic material such as nickel, gold, copper or silver in order to reduce friction of the surface to promote sliding of an archwire relative to the brackets during patient treatment and/or to enhance esthetics.

It is a primary object of the present invention to provide orthodontic brackets which are self-ligating and which are entirely or partially formed of a shape memory metallic alloy or non-metallic resin or polymer type material, including nickel-titanium materials, so as to allow flexibility of at least one of each pair of opposing tie wings when the base is securely bonded to the tooth or welded to a band that is cemented to the tooth. Further, the shape memory material allows the components of the bracket to exhibit super elasticity such that at least one of each pair of opposing tie wings may be flexed to permit insertion and removal of an archwire therebetween and thereafter immediately recover to its predetermined configuration and position to retain the archwire in the slot defined between each pair of opposing tie wings.

It is another object of the invention to provide self-ligating orthodontic brackets formed at least partially of a shape memory material which include two pair of opposing tie wings wherein at least one of each pair of tie wings includes a recess or area of reduced thickness to facilitate flexing of the at least one tie wing to permit insertion or removal of an archwire through an opening between the tie wings relative to an archwire guide slot afterwhich the tie wings close relative to one another.

It is also an object of the invention to provide self-ligating orthodontic brackets formed at least partially of a shape memory material wherein at least one of each of two pair of opposing tie wings may be moved to permit insertion and/or removal of an archwire therebetween and thereafter recover to a predetermined position and wherein at least one of each pair of tie wings includes a flange which extends toward the opposing tie wing to thereby normally retain an archwire within an archwire guide slot defined between the tie wings.

It is another object of the present invention to provide twin tie wing styled nickel-titanium or other shape memory material orthodontic brackets which include two pair of opposing tie wings each of which defines an archwire slot therebetween and wherein the pairs of tie wings are spaced relative to one another such that the brackets may be used in their position for initial treatment wherein an archwire may only pass between one pair of tie wings and thereafter may be adjusted such that the archwire passes through both pair of tie wings into the archwire guide slots as treatment progresses.

It is yet a further object of the present invention to provide nickel-titanium or other shape memory type orthodontic brackets which may be coated with metallic or non-metallic materials in such a manner as to reduce friction to thereby further facilitate the sliding movement of an archwire relative to the brackets during patient treatment and/or to enhance esthetics.

It is also an object of the present invention to enhance the aesthetic appearance of orthodontic brackets by providing nickel-titanium alloy or other shape memory material orthodontic brackets which may be coated in various colors to promote style depending on patient preferences.

The flexibility of the nickel-titanium or other shape memory self-ligating brackets with their small compact twin design will make them easy to use in the small confines of a patient's mouth which will give the Orthodontist additional treatment options of using ligatures to hold archwires in place in the bracket slots, and these brackets will solve the limitations of current self-ligating brackets.

The small compact flexible tie wing brackets of the invention, with and without a coating, will permit Orthodontists to overcome the many challenges they face during treatment and alignment of a patient's teeth and will make the patient's visits to the Orthodontist to have their braces adjusted a much less complicated process and overall more comfortable and quicker, resulting in making the overall treatment experience a more pleasant one while achieving superior results for the patient.

BRIEF DESCRIPTION OF THE DRAWINGS

A better understanding of the invention will be had with reference to the accompanying drawings wherein.

DESCRIPTION OF THE PREFERRED EMBODIMENTS

Figure 1:
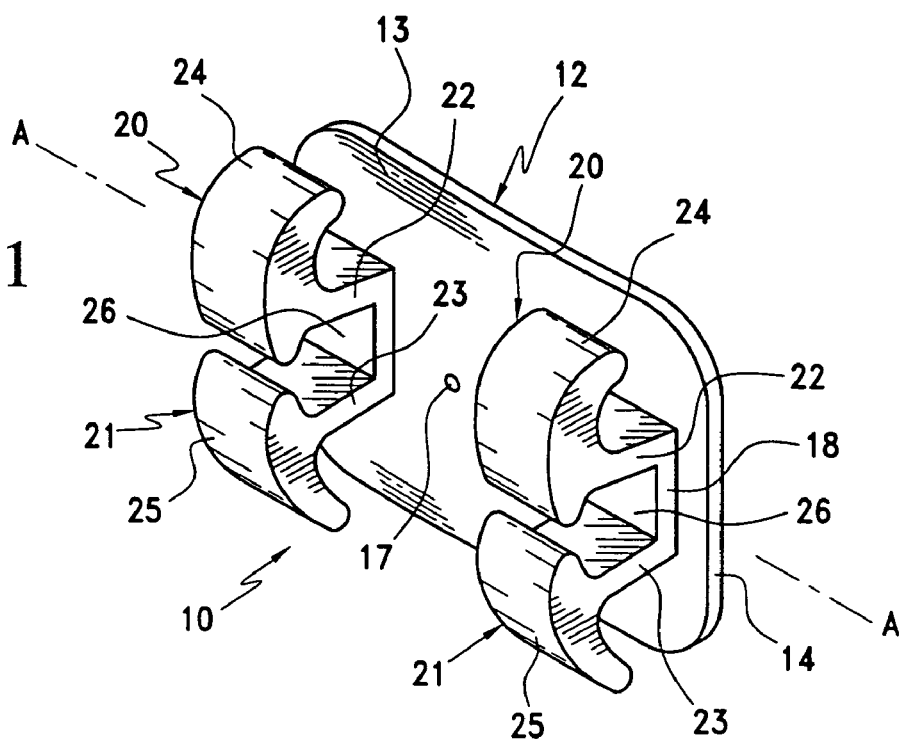
FIG. 1 is a front perspective view of an orthodontic bracket of the present invention.
Figure 2A:
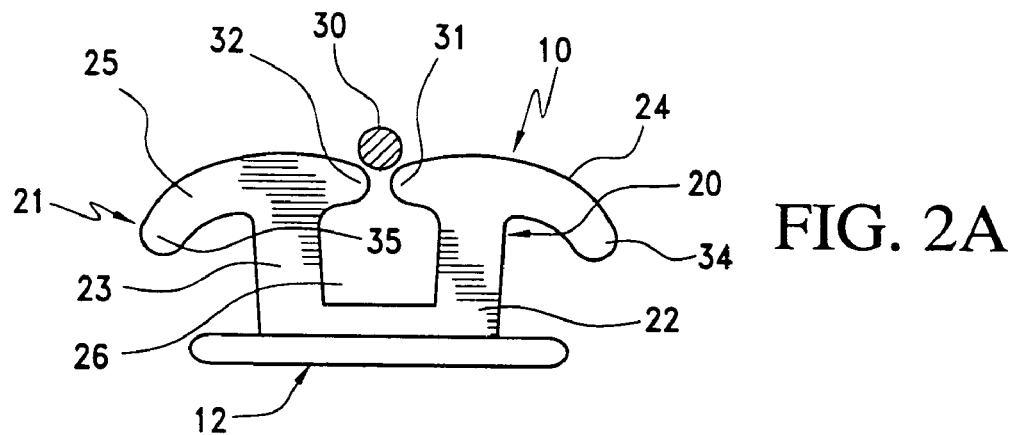
FIG. 2A is a side elevational view showing a first embodiment of the invention wherein both of the opposing tie wings are unflexed before insertion of an archwire relative to the archwire guide slot defined between the opposing tie wings of the bracket of FIG. 1.
Figure 2B:
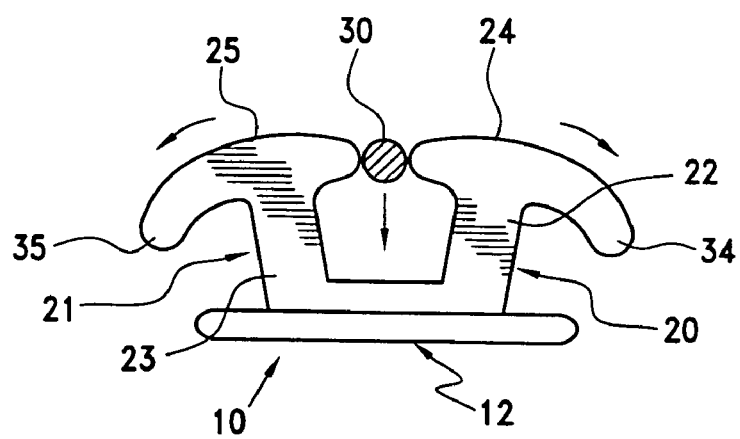
FIG. 2B is a side elevational view of the bracket of FIG. 2A showing both tie wings moved to permit insertion of an archwire therebetween.
Figure 2C:
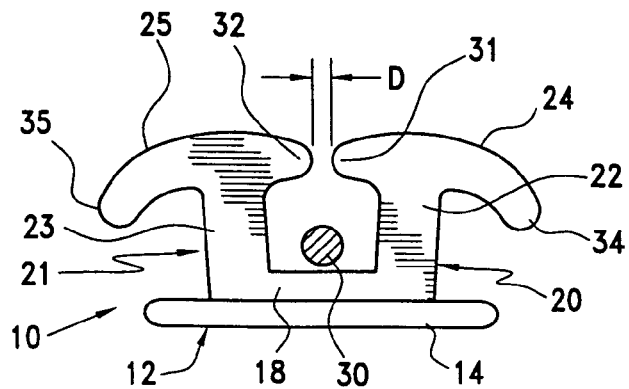
FIG. 2C is a side elevational view of the bracket of FIG. 2A illustrated with an archwire being seated within an archwire guide slot defined between the two opposing tie wings.

With continued reference to FIGS. 1–2C, a first embodiment of orthodontic bracket 10 of the present invention includes a contoured base 12 having a front surface 13 and tooth engaging surface 14. The rear surface 14 is generally slightly concavely contoured so as to match the surface contour of a patient's tooth.

The orthodontic bracket further includes two pair of spaced opposing tie wings 20 and 21 which are shown as being spaced on opposite sides of a central recess 17 which is formed generally centrally of the front surface of the bracket base 12. The recess 17 is used to facilitate alignment of the bracket relative to a patient's tooth using an instrument such as a Boone gauge. As opposed to the recess 17, a linear groove 17B may be provided in the front surface of the bracket base for facilitating alignment, see FIG. 6.

Each bracket includes a base portion 18 from which extend the tie wings 20 and 21. Each opposing tie wing includes a post 22 and 23, respectively, which extend from the base portion 18 to a head portion 24 and 25, respectively. Each pair of the generally parallel posts 22 and 23 define an archwire guide slot 26 of approximately 0.018 to 0.022 inch therebetween of a size to slidingly engage an archwire, such as shown at 30 in FIG. 2C.

The shape memory brackets of the present invention are self-ligating. That is, at least one or a portion of one of the tie wings is formed of a shape memory material. In the embodiment shown in FIGS. 1, 2A, 2B and 2C, both of the opposing pair of tie wings 20 and 21 are formed of a material which allows the tie wings to flex, as shown and illustrated in FIG. 2B, to permit insertion or removal of the archwire 30 relative to the archwire guide slot 26. In preferred embodiments, brackets of the present invention are formed of a shape memory material such as a nickel-titanium material both along the base and the tie wings. This material exhibits superelasticity and, therefore, shape memory, such that when the posts 22 and 23 are flexed from a predetermined or rest position, as shown in FIG. 2A, the head portions 24 and 25 of each tie wing separate, as shown in FIG. 2B, to permit the insertion or removal of the archwire. Once force is removed, the posts return to their normal predetermined position, as shown in FIG. 2C. Shape memory metallic alloys, non-metallic resins, polymer type materials, and other material that exhibit a shape memory may be used.

To securely retain an archwire within the archwire guide slot 26, each head portion, as shown in FIG. 2A, may include a pair of arcuate inner opposing flanges 31 and 32 which are spaced at a distance "D" of approximately 0.010–0.012 inch which is smaller than the diameter of the archwire. In some embodiments, the inner flanges may actually touch one another such that the distance "D" is zero.

The tie wings further include outer flanges 34 and 35 which may be used in a conventional manner to secure archwires with ligature wires and other attachments during patient treatment, as is necessary. In the preferred embodiments, the entire outer surface of the head portion is shown as being generally convex with the inner flanges 31 and 32 tapering downwardly and inwardly relative to one another.

As opposed to each tie wing including a base portion, such as illustrated at 18, it is possible that the tie wings 22 and 23 are formed such that the posts extend upwardly from the front surface 13 of the bracket base 12.

Figure 3A:
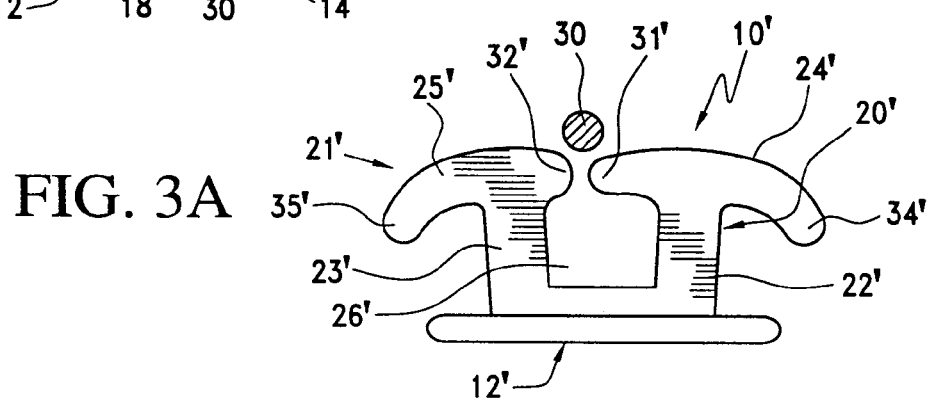
FIG. 3A is a view similar to FIG. 2A except of an embodiment wherein only one of each opposing pair of tie wings is formed of a shape memory material.
Figure 3B:
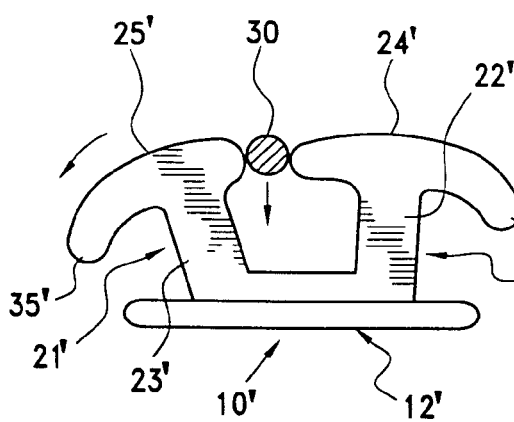
FIG. 3B is a side elevational view of the bracket of FIG. 3A showing only one tie wing being moved to permit insertion of an archwire within the archwire guide slot between the opposing tie wings.
Figure 3C:
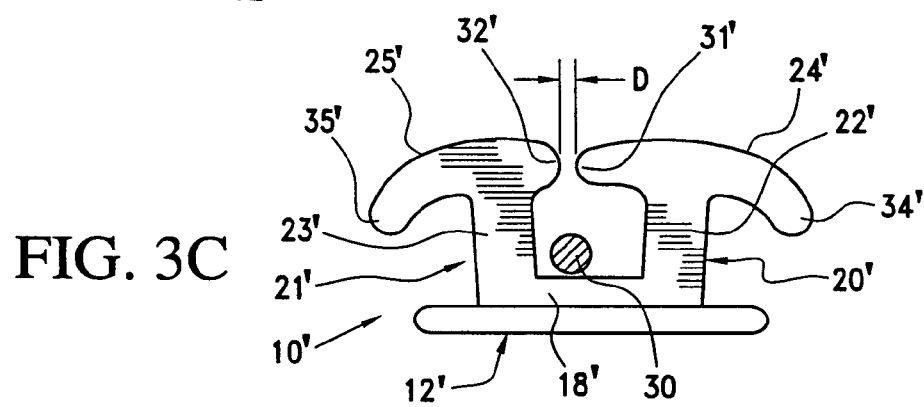
FIG. 3C is a side elevational view of bracket of FIG. 3A showing the archwire seated in the slot between the tie wings.

An alternate embodiment of orthodontic bracket 10' of the invention is shown in FIGS. 3A, 3B and 3C. In this embodiment, only one or a portion of each pair of opposing tie wings 20' and 21' is formed of a shape memory material so as to be flexed from a predetermined or rest position, as shown on FIG. 3A, to a spaced position, as shown by the arrow in FIG. 3B, to permit insertion or removal of an archwire 30 relative to the archwire slot 26'. Thereafter the tie wing 21' will return to its predetermined or rest position, as shown in a FIG. 3C. The bracket 10' of this embodiment is otherwise the same as the bracket 10 previously described and includes tie wing posts 22' and 23', base 12', head portions 24' and 25' having inner opposing flanges 31' and 32' and outer flanges 34' and 35'. The inner flanges define an opening "D" as previous defined. Also one of the inner flanges may be larger than the opposing inner flange, although they may be of equal size and shown in FIGS. 1–2C. As shown in FIGS. 3A–3C, flange 31' is larger than flange 32'.

Figure 4:
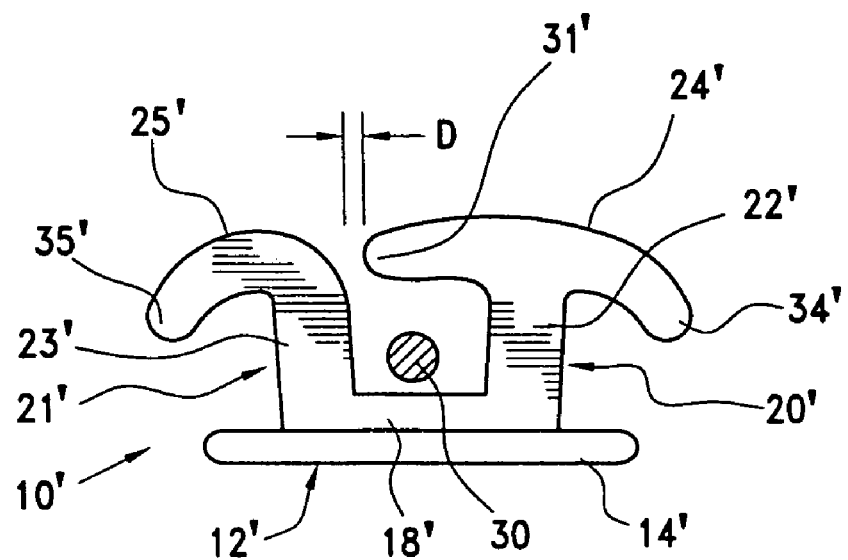
FIG. 4 is a view of a modified form of the bracket shown in FIGS. 3A–3C.

A modification of the embodiment of orthodontic bracket of FIGS. 3A–3C is shown in FIG. 4. In this embodiment, only one of each pair of opposing tie wings 20' and 21' includes an inner flange which defines the opening "D" as previously defined. As shown, there is no inner flange associated with tie wing 21'. The functioning of the bracket is otherwise the same as described with respect to FIGS. 3A–3C.

Figure 5:
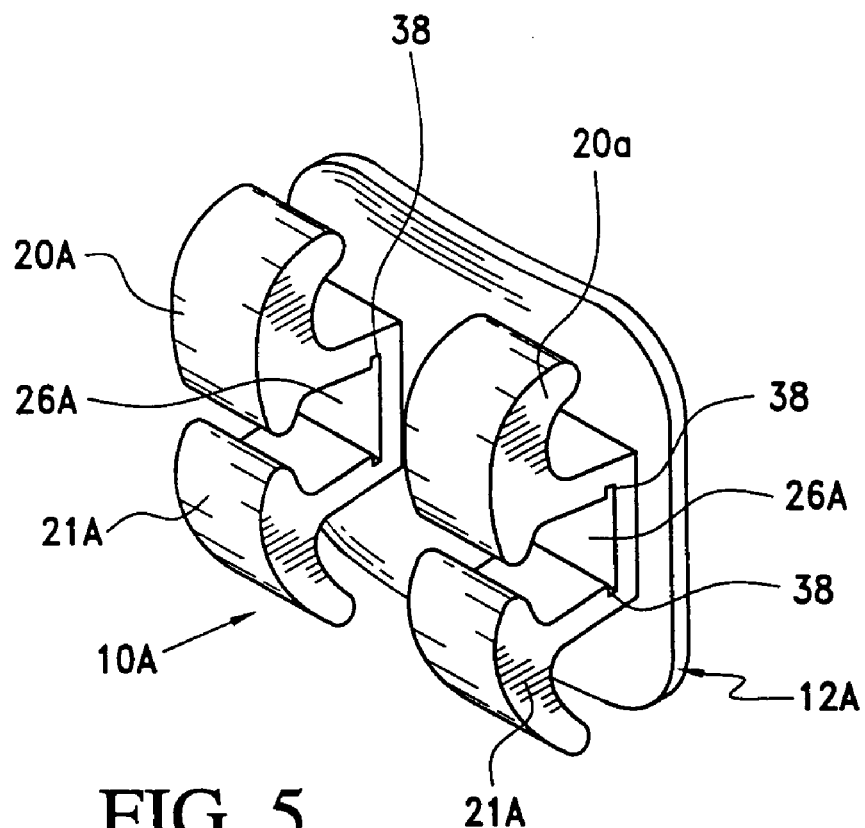
FIG. 5 is a front perspective view of another embodiment of orthodontic bracket according to the invention.

As illustrated in FIG. 5, to further promote the flexing of the tie wing and/or wings relative to one another, grooves, such as shown at 38 may be provided adjacent the inner portion of each of the posts. This facilitates a flexing of the tie wings at the area of reduced thickness. The bracket 10A of this embodiment is shown as being smaller than that of the embodiment of FIG. 1 such that the opposing pair of tie wings are more closely spaced. The bracket includes a base 12A and tie wings 20A and 21A defining archwire guide slots 26A therebetween. The provision of a groove to promote flexing may also be used in the embodiment of the invention shown in FIGS. 1, 2A, 3A, 4, 6, and 7.

Figure 6:
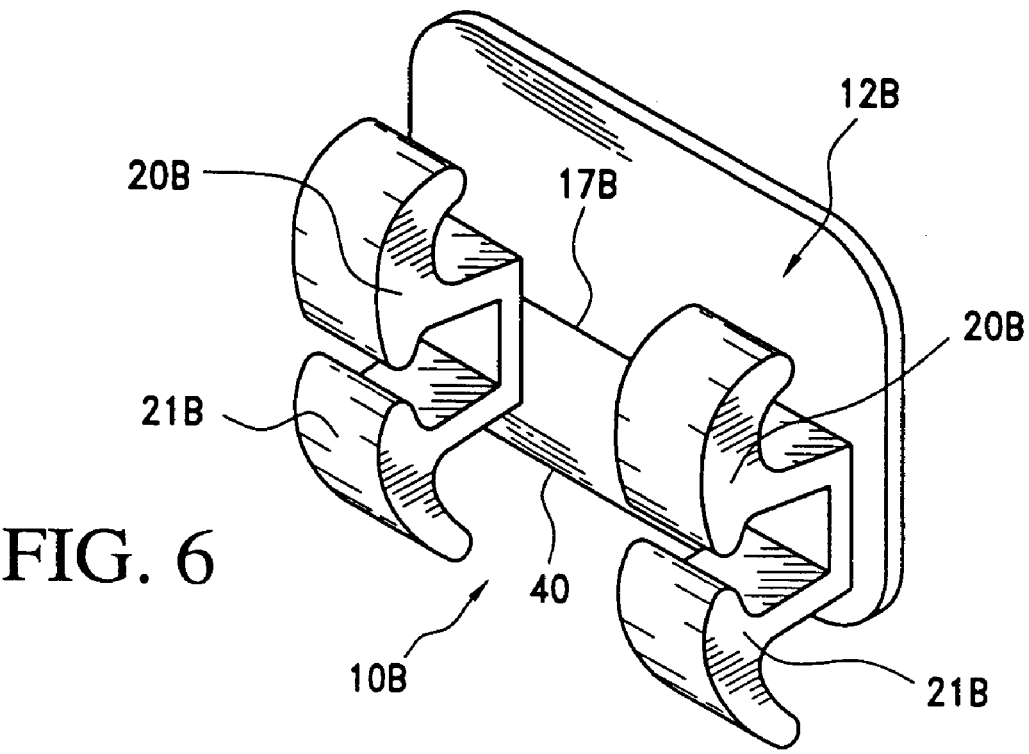
FIG. 6 is a front perspective view of a further embodiment of an orthodontic bracket in accordance with the invention.
Figure 7:
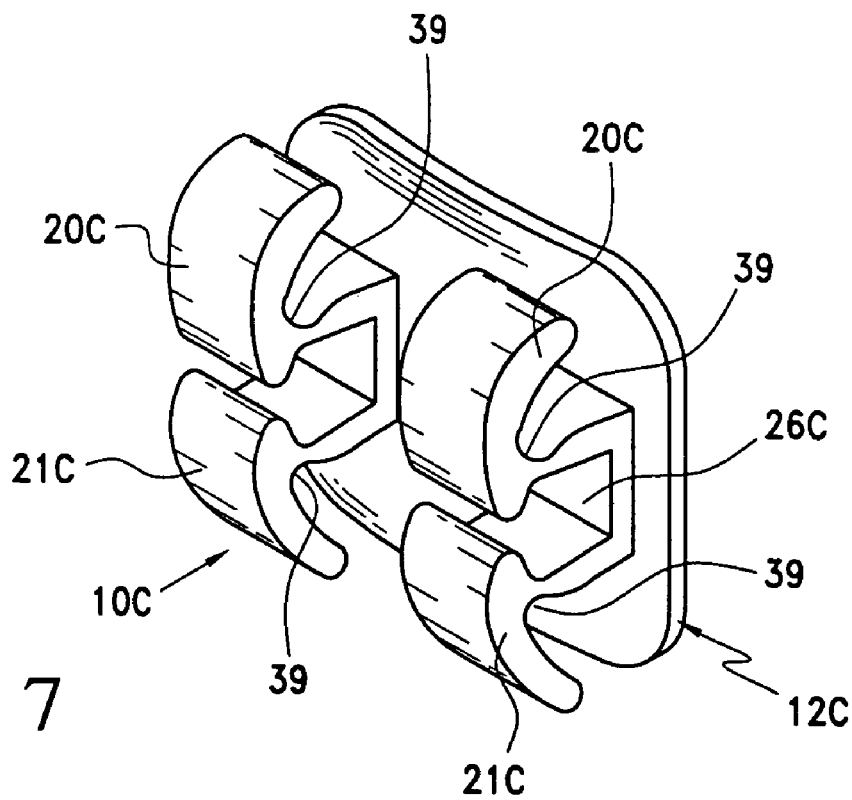
FIG. 7 is a front perspective view of an additional embodiment of orthodontic bracket in accordance with the invention.

As shown in FIG. 7, also to promote flexing of the tie wing and/or tie wings relative to one another, the thickness of one or more of the tie wing posts, may be reduced in an area such as shown at 39. The bracket 10C of this embodiment is shown as being smaller than that of the embodiment of FIG. 1 such that the opposing pair of tie wings are more closely spaced. The bracket includes a base 12C and tie wings 20C and 21C defining archwire guide slot 26C therebetween. The provision of reduced thickness of the tie wing posts to promote flexing may also be used in the embodiment of the invention shown in FIGS. 1, 2A, 3A, 4, 5 and 6.

As the present invention utilizes a twin tie wing configuration formed of a nickel-titanium or other material exhibiting shape memory, the bracket slot and tie wings of the bracket exhibit some degree of flexibility. The base 12 has a bonding pad with mesh such that the bracket may be bonded securely to a patient's tooth or welded to a band cemented to the tooth. Further, with the structure of the present invention, it is possible to apply the bracket to extremely twisted or crooked teeth wherein only two tie wings may be appropriately aligned with the tooth to receive an archwire. During initial treatment, the archwire may be seated within a single archwire guide slot defined by one pair of opposing tie wings until such a time as a tooth is moved to a position wherein the archwire may be aligned within both pair of tie wings and seated into the bracket archwire guide slots. In this respect, it should be noted that tie wings of the present invention define archwire guide slots which are preferably axially aligned relative to one another along a line A—A as shown in FIG. 1.

With reference to FIG. 6, another embodiment of the invention is shown. In this embodiment, the bracket 10B is formed of the same shape memory material having two pair of opposing tie wings 20B and 21B which extend from a base 12B. However, the tie wings extend upwardly from a position more closely spaced to a gingival edge 40 of the bracket base. This structure permits correct bonding of brackets on short or gingivally displaced teeth. In this embodiment, a horizontal recess alignment guide 17B is shown, as opposed to the recess 17 shown in FIG. 1. In this embodiment, either one or both of the opposing tie wings may be flexed as previously described. The provision of the bracket tie wings extending upward from a position close to a gingival edge of the bracket base may also be used in the embodiment of the invention shown in FIGS. 1, 2A, 3A, 4, 5 and 7.

Due to the shape memory material from which the brackets of the present invention are formed, very low friction surfaces are presented for guidingly engaging the archwire. The lower friction between the bracket and the archwire, the more smoothly and easily the archwire will function to move a patient's tooth to a desired position, thus facilitating patient treatment. In this respect, the present invention also provides for further decreasing the frictional surface resistance of the brackets by allowing the brackets to be coated with other materials. By way of example, except the bonding base pad or mesh, the surface of the brackets including the tie wings and base, especially in the area of the archwire guide slots, may be plated or electroplated with metallic elements such as nickel, gold, copper, or silver. As opposed to a plating with metallic material, the brackets, except the bonding base pad or mesh may be coated with different plastics including polytetrafluoroethylene (PTFE) including Teflon™, thermosetting polymers or other polymers, with or without coupling agents which are specifically provided to create a smoother surface and thereby reduce friction.

In accordance with the invention, the surface treatments may also include coloring agents. It may be desired to increase the aesthetic appearance of new orthodontic brackets by including coloring agents which would present hues of gold, tooth color, red, green, blue or other colors.

To facilitate the coating process, the surface of the orthodontic bracket and the tie wings may be chemically etched or mechanically pitted such as by blasting to create a surface roughness to facilitate bonding of a coating material.

The orthodontic brackets of the present invention are preferably used with archwires which are also formed of a nickel-titanium material, such as Nitinol™, which is a superelastic metallic material which exhibits flexibility and has a shape memory.

The flexibility of the nickel-titanium, or other material exhibiting shape memory, self-ligating brackets of the present invention and the small compact twin tie wing design of the invention make it easy for the brackets to be used in particularly difficult areas to access and small confines within the patient's mouth and may be used with or without the need for conventional plastic or metal ligatures to hold the archwire in place during patient treatment. Additionally, elastomeric colors, elastomeric ties, elastomeric power chains, directional elastics and/or various attachments may be added to the bracket to facilitate a smooth orthodontic treatment. The present invention promotes efficient patient treatment by further facilitating the mechanical movement between the archwire and the orthodontic brackets which will reduce patient treatment time and therefore increase patient comfort.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

I claim:

1. A self-ligating orthodontic bracket comprising: a unitary body structure including a base having front and rear surfaces, two pair of spaced opposing tie wings, each tie wing having a post member extending from said front surface of said base in spaced relationship with respect to a post member of an opposing tie wing, each pair of opposing tie wing posts define an archwire guide slot therebetween of a first dimension to slidingly receive an archwire therein, each pair of opposing tie wings including head portions having outward extending flanges and at least one of each pair of opposing tie wings including an inwardly extending flange, said inwardly extending flange being in a predetermined positioned relative to the opposing tie wing to retain an archwire within said archwire guide slots, and at least a portion of the bracket being formed of a material such that at least one of each pair of opposing tie wings exhibits flexibility and shape memory effect allowing relative movement between said at least one of each pair of opposing tie wings and the opposing tie wing to permit insertion or removal of an archwire relative to said archwire guide slots afterwhich said at least one of each pair of opposing tie wings returns to its predetermined position.

2. The self-ligating orthodontic bracket of claim 1 in which each of said opposing tie wings exhibits flexibility and shape memory effect.

3. The self-ligating orthodontic bracket of claim 1 in which each head portion includes an inwardly extending flange.

4. The self-ligating orthodontic bracket of claim 1 in which said base and said tie wings are formed of a material which exhibits shape memory effect.

5. The self-ligating orthodontic brackets of claim 3 wherein said material is a nickel-titanium material.

6. The self-ligating orthodontic brackets of claim 2 wherein said material is a nickel-titanium material.

7. The self-ligating orthodontic bracket of claim 1 wherein said material is a nickel-titanium material.

8. The self-ligating orthodontic bracket of claim 1 including an area of reduced thickness adjacent to a base of at least one of said posts of said tie wings to facilitate flexing.

9. The self-ligating orthodontic bracket of claim 1 in which at least one of said posts has an area of reduced thickness to promote flexing of said at least one tie wing.

10. The self-ligating orthodontic bracket of claim 1 including an alignment recess formed centrally in said front surface of said base.

11. The self-ligating orthodontic bracket of claim 1 including a horizontal alignment recess formed centrally in said front surface of said base.

12. The self-ligating orthodontic bracket of claim 1 in which said two pair of opposing tie wings are aligned with one another and spaced adjacent a gingival edge of said base of said bracket.

13. The self-ligating orthodontic bracket of claim 12 including an alignment recess formed centrally in said front surface of said base.

14. The self-ligating orthodontic bracket of claim 12 including a horizontal alignment recess formed centrally in said front surface of said base.

15. The self-ligating orthodontic bracket of claim 1 in which said base and said tie wings are coated with a coating material selected from a group of materials consisting of metallic materials, non-metallic materials, and polymers.

16. The self-ligating orthodontic bracket of claim 15 wherein said non-metallic polymers are thermosetting polymers.

17. The self-ligating orthodontic bracket of claim 15 in which said coating material includes a coloring agent.

18. The self-ligating orthodontic bracket of claim 1 in which at least said archwire guide slot of each of said tie wings is coated with a coating material selected from a group of materials exhibiting a low coefficient of friction consisting of metallic materials and non-metallic polymers.

19. The self-ligating orthodontic bracket of claim 18 wherein said non-metallic polymers are thermosetting polymers.

20. The self-ligating orthodontic bracket of claim 18 in which said coating material includes a coloring agent.

21. The self-ligating orthodontic bracket of claim 18 wherein the coating material is a material applied by electroplating.

22. The self-ligating orthodontic bracket of claim 1 wherein said material is selected from a group of materials exhibiting shape memory consisting of metallic materials and non-metallic materials.

23. A self-ligating orthodontic bracket comprising: a unitary body structure including a base having front and rear surfaces, two pair of spaced opposing tie wings, each tie wing having a post member extending from said front surface of said base in spaced relationship with respect to a post member of an opposing tie wing, each pair of opposing tie wing posts define an archwire guide slot therebetween of a first dimension to slidingly receive an archwire therein, each pair of opposing tie wings including head portions having inner opposing flanges and outward extending flanges, said inner opposing flanges being in a predetermined positioned relative to one another to retain an archwire within said archwire guide slots, and at least a portion of the bracket being formed of a material such that at least one of each pair of opposing tie wings exhibits flexibility and shape memory effect allowing said inner opposing flanges to move relative to one another to permit insertion or removal of an archwire relative to said archwire guide slots afterwhich said at least one of each pair of opposing tie wings returns to its predetermined position.

* * * * *